United States Patent

Miyajima et al.

Patent Number: 5,282,869
Date of Patent: Feb. 1, 1994

[54] ARTIFICIAL KNEE JOINT

[75] Inventors: Hideyuki Miyajima, Kyoto; Toyoji Ueo, Matsue, both of Japan

[73] Assignee: Kyocera Corporation, Kyoto, Japan

[21] Appl. No.: 953,752

[22] Filed: Sep. 29, 1992

Related U.S. Application Data

[63] Continuation of Ser. No. 777,803, Oct. 17, 1991, abandoned.

[30] Foreign Application Priority Data

Oct. 24, 1990 [JP] Japan .................. 2-286596

[51] Int. Cl.$^5$ .............................................. A61F 2/38
[52] U.S. Cl. ................................................. 623/20
[58] Field of Search ........................................ 623/20

[56] References Cited

U.S. PATENT DOCUMENTS 4,355,429 10/1982 Mittelmeier et al. .
4,728,332 3/1988 Albrektsson .
4,959,071 .../.990 Brown et al. .................. 623/20

FOREIGN PATENT DOCUMENTS 0268216 5/1988 European Pat. Off. .
0294298 12/1988 European Pat. Off. ......... 623/20

Primary Examiner—David Isabella
Assistant Examiner—Debra S. Brittingham
Attorney, Agent, or Firm—Spensley Horn Jubas & Lubitz

[57] ABSTRACT

An artificial knee joint comprising a femoral component secured to the distal portion of a femur and a tibial component secured to the proximal portion of a tibia so that both the components are brought into sliding contact with each other via sliding surfaces, wherein the femoral component is provided on a rear central section of the sliding surface with a spherical or elliptical convex sliding surface and the tibial component is provided on the rear central section of the sliding surface with a spherical or elliptical concave sliding surface so that both the sliding surfaces are brought into sliding engagement when the artificial knee joint comprising the femoral and tibial components is bent deeply, whereby a person with this artificial knee joint can take a deep knee bending posture when sitting, which cannot be attained by conventional technology.

6 Claims, 4 Drawing Sheets

ARTIFICIAL KNEE JOINT

This is a continuation of application Ser. No. 07/777,803 filed on Oct. 17, 1991, now abandoned.

BACKGROUND OF THE INVENTION

1. Field of the Invention

The present invention relates to an artificial knee joint used to properly restore knee joints significantly deformed by chronic rheumatism or osteo-arthritis, or those broken in traffic accidents or during disasters.

2. Prior Art

A conventional artificial knee joint replacement treatment is conducted by cutting the distal portion of the femur and the proximal portion of the tibia of a knee joint damaged or broken by disease or accident, and by inserting and securing a femoral component and a tibial component to the distal portion of the femur and the proximal portion of the tibia respectively so that the femoral component slides on the sliding surface of the tibial component, thereby allowing the knee joint to be bent.

When the femoral component of the artificial knee joint slides on the tibial component as described above to perform a knee bending movement, if the fermoral component 1 of the artificial knee joint rotates on the front upper surface of the tibial component 2 of the knee joint as shown in FIG. 5, the movable range of the femoral component 1 is limited, preventing a person with the artificial knee joint from taking a deep knee bending posture when sitting and thus causing inconvenience during his daily life. To solve this problem, a method has been taken wherein a post provided on the tibial component of an artificial knee joint controls the femoral component to ensure a bending movement between the femur and the tibia (for example, Japanese Laid-open Patent Application No. 63-132651). In the above-mentioned case of the method wherein the post provided on the tibial component controls the femoral component at the time of the bending of the artificial knee joint to securely offer a sufficient movable range to the artificial knee joint, the post receives all loads and undergoes stress concentration. The post is, therefore, deformed or broken and cannot attain desired functions.

SUMMARY OF THE INVENTION

The object of the present invention is to provide an artificial knee joint which can solve the above-mentioned problems. The general concept of the present invention is to extend the main joint surfaces by providing portions on the rear sides of the main joint surfaces to receive the loads from both the femoral and tibial components so that deep bending is attained by using the newly provided rear side joint surfaces when the femoral and tibial components reach a knee bending relation. These additional joint surfaces are realized by providing a convex sliding surface on a rear central section of the femoral component and by also providing a concave sliding surface on the tibial component so that both the sliding surfaces are brought into sliding engagement. Both the sliding surfaces begin sliding when the femoral and tibial components reach a knee bending relation. This sliding movement continues until a deep bending angle of 135° or more is attained, allowing a person with the artificial knee joint to take a deep knee bending posture when sitting, which cannot be attained by the above-mentioned conventional technology. In addition, unlike the above-mentioned prior art which receives the whole stress by a part of a single component, such as the above-mentioned post, these newly provided joint surfaces undergo stress distribution, thereby preventing the components from being deformed or broken.

The present invention is detailed below referring to the attached drawings.

DETAILED DESCRIPTION OF THE PREFERRED EMBODIMENTS

Figure 1A:
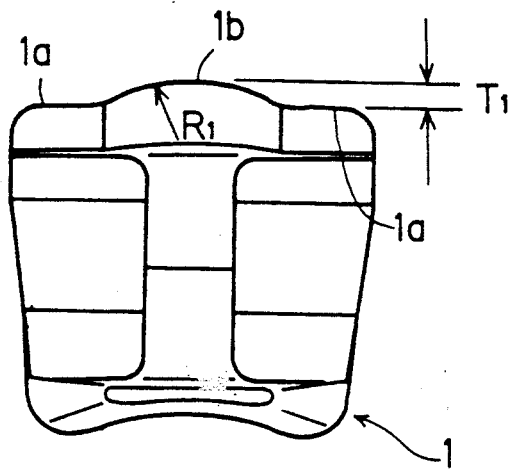
FIGS. 1 (A), 1 (B) and 1 (C) are respectively a plan view, a front view and a side view of a femoral component of the artificial knee joint related to an embodiment of the present invention.
Figure 1B:
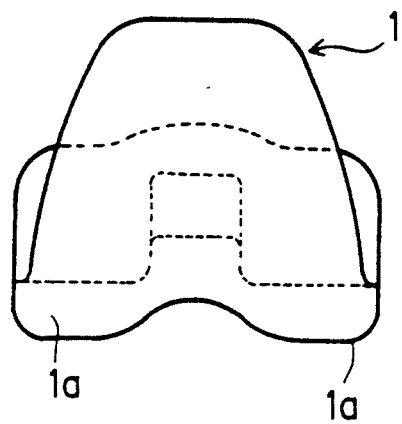
Figure 1C:
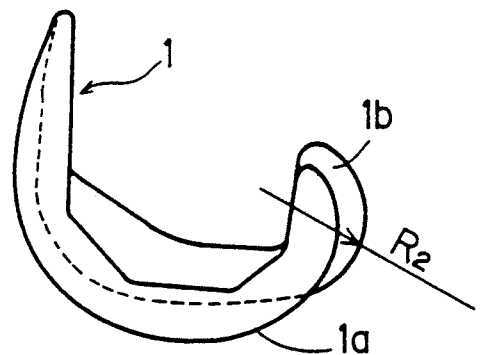

Referring to FIGS. 1 (A), 1 (B) and 1 (C) being respectively a plan view, a front view and a side view of the femoral component 1 of the artificial knee joint of the present invention, in order to conduct backward bending movement, a convex sliding surface 1b with height $T_1$, backward spherical or elliptical convex curvature $R_1$ and upward spherical or elliptical convex curvature $R_2$ is formed on the femoral component 1 at the rear central sliding section of the main joint surfaces 1a, 1a which receive loads.

Figure 2A:
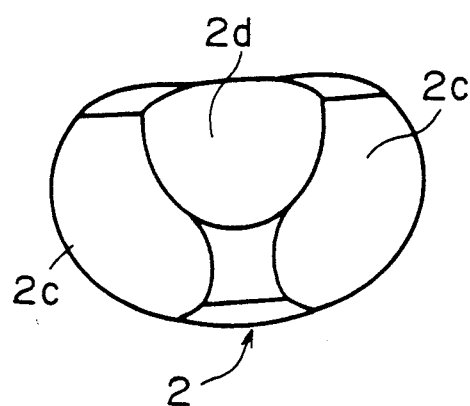
FIGS. 2 (A), 2 (B) and 2 (C) are respectively a plan view, a front view and a side view of a tibial component of the artificial knee joint related to an embodiment of the present invention.
Figure 2B:
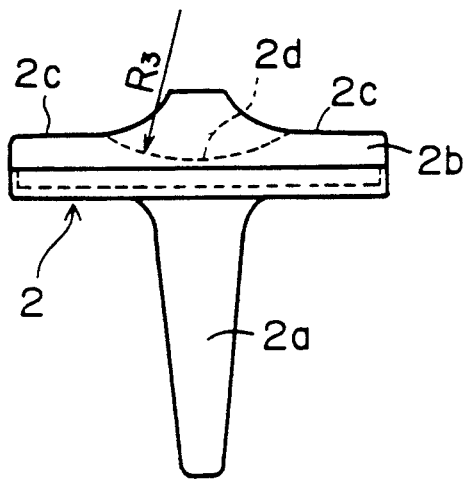
Figure 2C:
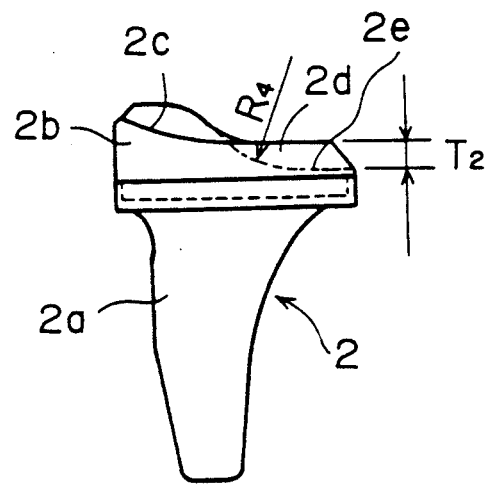

Referring to FIGS. 2 (A), 2 (B) and 2 (C) being respectively a plan view, a front view and a side view of the tibial component 2 of the artificial knee joint of the present invention, the tibial component 2 is composed of a tray member 2a which supports a load and a sliding member 2b which slides with the femoral component 1. On the sliding member 2b, a concave sliding surface 2d with depth $T_2$, spherical or elliptical lateral concave curvature $R_3$ and downward spherical or elliptical concave curvature $R_4$ is formed at the rear central sliding surface of the main joint surfaces 2c, 2c which receive loads, to accommodate the convex sliding surface 1b of the femoral component 1.

The femoral component 1 and the tray member 2a of the tibial component 2 are made of ceramics (alumina, zirconia, etc.), metals (stainless steel, COP, Co-Cr-Mo alloy, pure Ti, Ti alloys, etc.) or materials made of carbon fiber or synthetic resin, or carbon fiber bound to a desired thicknesses. Alumina, apatite, glass ceramics, TiN, $TiO_2$, etc. can be coated on the bone contacting surfaces of these materials. The sliding member 2b of the tibial component 2 is made of synthetic resin such as high-density polyethylene to ensure smooth sliding with the femoral component 1.

Figure 3:
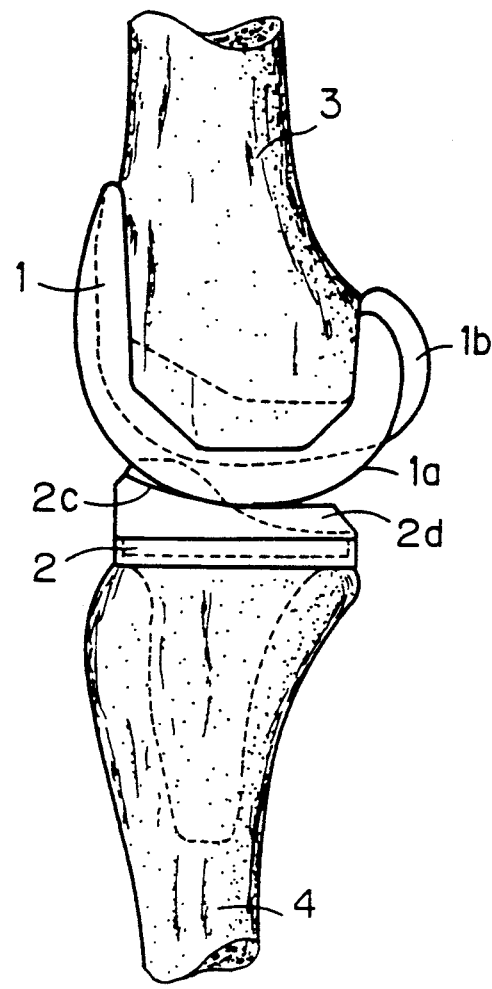
FIG. 3 is a side view illustrating a stretching condition of a knee joint wherein the femoral and tibial components of the artificial knee joint of an embodiment of the present invention are secured to the distal portion of the femur and the proximal portion of the tibia of the knee joint respectively.
Figure 4:
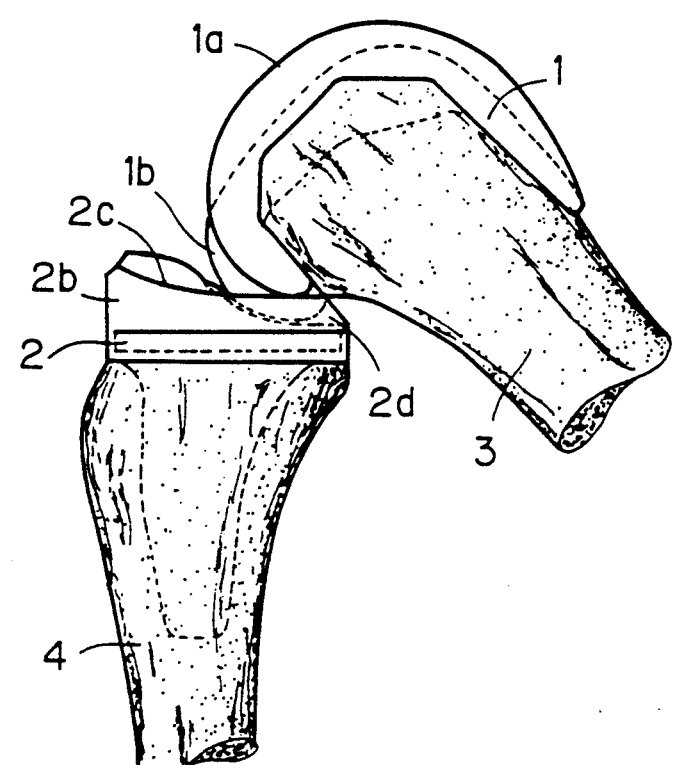
FIG. 4 is a side view illustrating a bending condition of a knee joint wherein the femoral and tibial components of the artificial knee joint of an embodiment of the present invention are secured to the femur and tibia of the knee joint.
Figure 5:
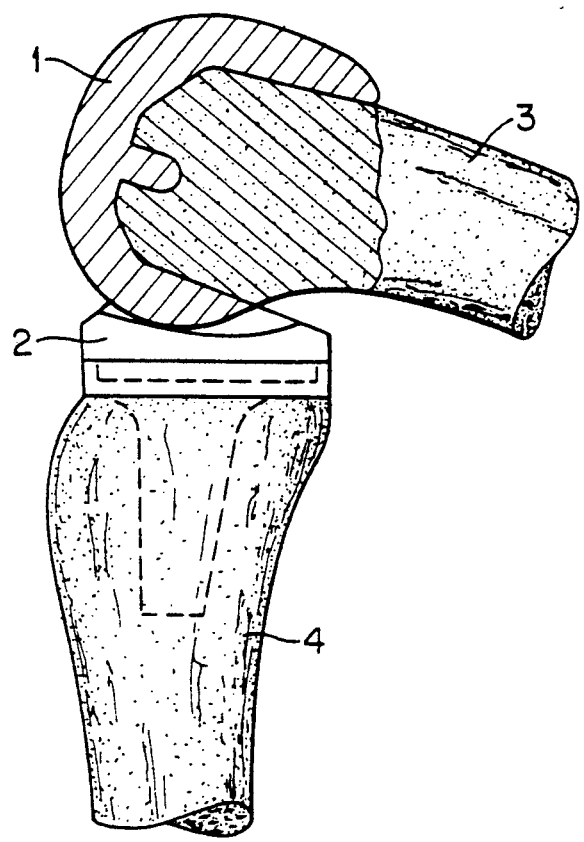
FIG. 5 is a view similar to FIG. 4, illustrating a conventional technology.

FIG. 3 illustrates a stretching condition of a knee joint wherein the femoral component 1 and the tibial component 2 are secured to the distal portion of the femur 3 and the proximal portion of the tibia 4 respectively. In this condition, a load to the knee joint is received by the main joint surfaces 1a, 1a of the femoral component 1 and the main joint surfaces 2c, 2c of the tibial component 2. When the knee joint is rotated and bent from this condition, the convex sliding surface 1b of the femoral component 1 is accommodated or fitted in the concave sliding surface 2d formed at the rear central sliding section of the sliding member 2b of the tibial component 2 as shown in FIG. 4. Therefore, the femoral component 1 can perform smooth knee bending movement at the rear of the tibial componnet 2 without moving forward. The artificial knee joint of the present invention can thus increase its back-and-forth movement range up to 135° or more, wider than the movement range of about 90° to 100° attained by conventional artificial knee joints, thereby allowing a person with the artificial knee joint to take a deep knee bending posture when sitting.

In this condition of the present invention, the relationship between the height $T_1$ of the convex sliding surface of the femoral component shown in FIG. 1 (A) and the depth $T_2$ of the concave sliding surface of the tibial component shown in FIG. 2 (C) should be $T_1 \leq T_2$, the relationship between the curvatures $R_1$ and $R_3$ should be $R_1 \leq R_3$, and the relationship between the curvatures $R_2$ and $R_4$ should be $R_2 \leq R_4$. Their actual values should be $T_1 = 2$ to 10, $T_2 = 2$ to 11, $R_1 = R7$ to R50, $R_2 = R7$ to R30, $R_3 = R7$ to R55 and $R_4 = R7$ to R35. With these values, the main joint surfaces can receive the load even during bending movement. In addition, the knee joint can perform rotation movement. Furthermore, by providing a flat section 2e at the rear section of the concave sliding surface 2d of the tibial component 2, knee bending movement is possible at a further backward position, thereby restoring the functions of the artificial knee joint to those inherent to a natural knee joint.

As described above, by forming a spherical or elliptical convex sliding surface on the rear central sliding section of the femoral component and by also forming a spherical or elliptical concave sliding surface on the rear central sliding section of the tibial component, smooth rotation movement is possible at the rear of the tibial component at the time of knee joint bending and stress can be distributed, ensuring a larger movable range. Therefore, after the artificial knee joint of the present invention is installed, the same knee joint functions as those of a normal natural knee joint can be achieved, thereby greatly contributing to the welfare of the human beings.

We claim:

1. An artificial knee joint comprising:
   a femoral component to be secured to a distal portion of a femur, said femoral component having a femoral sliding surface and a convex load bearing surface provided in a rear central section of the femoral component and protruding beyond the femoral sliding surface;
   a tibial component to be secured to a proximal portion of a tibia, said tibial component having a tibial sliding surface for sliding engagement with said femoral sliding surface at a contact point and a concave load bearing surface provided in a rear central section of the tibial sliding surface for sliding engagement with the convex load bearing surface when said artificial knee joint is bent deeper than a predetermined flex angle from full extension of said artificial knee joint wherein said concave load bearing surface coacts with said convex load bearing surface protruding beyond the femoral proximal portion to move the contact point toward the rear edge of said tibial sliding surface as said knee joint is bent deeper than the predetermined flex angle.

2. An artificial knee joint comprising:
   a femoral component to be secured to a distal portion of a femur, said femoral component having a pair of main femoral joint surfaces and a rear central load-bearing sliding section between said main femoral joint surfaces, said central load-bearing sliding section having a convex sliding surface protruding from said main joint surfaces by a height $T_1$, said convex sliding surface further having a backward arcuate convex curvature $R_1$ and an upward arcuate convex curvature $R_2$; and
   a tibial component to be secured to a proximal portion of a tibia, said tibial component having a pair of tibial main joint surfaces and a concave sliding surface between said tibial main joint surfaces, said concave sliding surface being receded by a depth $T_2$ from said tibial main joint surfaces in proximity of a rear central area thereof, said concave sliding surface further having an arcuate lateral concave curvature $R_3$ and an arcuate downward concave curvature $R_4$, wherein the relationship between $T_1$ and $T_2$, between $R_1$ and $R_3$, and between $R_2$ and $R_4$ is defined as $T_1 \leq T_2$, $R_1 \leq R_3$, and $R_2 \leq R_4$ respectively so that said convex sliding surface is brought into sliding engagement with said concave sliding surface when said artificial knee joint is bent deeper than a predetermined flex angle from full extension of said artificial knee joint.

3. An artificial knee joint according to claim 2 wherein said concave sliding surface of said tibial component has a flat section disposed at the rear thereof.

4. An artificial knee joint according to claim 2 or 3, wherein $T_1 = 2$ to 10, $T_2 = 2$ to 11, $R_1 = R7$ to R50, $R_2 = R7$ to R30, $R_3 = R7$ to R55 and $R_4 = R7$ to R35.

5. An artificial knee joint comprising:
   a femoral component adapted to be secured to a distal portion of a femur, said femoral component having a pair of spaced arcuate femoral sliding surfaces and an arcuate convex load bearing surface provided in a rear central section of said femoral component between said femoral sliding surfaces and protruding beyond the femoral sliding surfaces; and
   a tibial component adapted to be secured to a proximal portion of a tibia, said tibial component having a pair of spaced arcuate tibial sliding surfaces for sliding engagement with said femoral arcuate sliding surfaces respectively at a contact point, and an arcuate concave load bearing surface provided on a rear central section of said tibial component between said tibial sliding surfaces for sliding engagement with said convex load bearing surface protruding beyond the femoral sliding surfaces when said artificial knee joint is flexed deeper than a predetermined flex angle from full extension of said artificial knee joint wherein said concave load bearing surface coacts with said convex load bearing surface to move the contact point rearwardly with respect to said tibial sliding surface.

6. An artificial knee joint according to claim 5 wherein said concave load bearing surface is generally recessed lower than said arcuate tibial sliding surfaces.